(12) United States Patent
Ishii

(10) Patent No.: US 6,242,609 B1
(45) Date of Patent: Jun. 5, 2001

(54) METHOD FOR MANUFACTURING A COLOR COUPLER USED IN A SILVER HALIDE PHOTOGRAPHIC LIGHT-SENSITIVE MATERIAL

(75) Inventor: Fumio Ishii, Hino (JP)

(73) Assignee: Konica Corporation (JP)

( * ) Notice: Subject to any disclaimer, the term of this patent is extended or adjusted under 35 U.S.C. 154(b) by 0 days.

(21) Appl. No.: 09/287,501

(22) Filed: Apr. 7, 1999

(30) Foreign Application Priority Data

Apr. 13, 1998 (JP) .................................................. 10-101023

(51) Int. Cl.⁷ ...................... C07D 249/16; C07D 231/08; C07D 487/04; C07C 229/60; C07C 229/70
(52) U.S. Cl. ........................ 548/262.4; 548/181; 548/206; 548/250; 548/254; 548/360.5; 548/379.1; 548/379.4; 548/510; 548/511; 548/530; 548/540; 548/110; 548/114; 560/27; 560/28; 560/34; 560/100; 562/467; 562/475; 564/84; 564/102; 564/155; 564/158; 564/161; 564/173; 564/174; 564/182; 564/184; 564/186; 564/190; 564/191; 564/192; 564/200; 564/211; 564/214; 564/218; 564/223; 564/442; 564/443; 568/774; 568/780; 568/784; 430/376; 430/385; 430/387; 430/389

(58) Field of Search ..................................... 430/376, 385, 430/387, 389; 548/360.5, 262.4, 368.7, 371.1, 379.1, 510; 560/100, 27; 562/467, 475; 564/84, 102, 155, 161, 192, 218, 442

(56) References Cited

FOREIGN PATENT DOCUMENTS

07304776 * 11/1995 (JP) .

* cited by examiner

*Primary Examiner*—Jane Oswecki
(74) *Attorney, Agent, or Firm*—Jordan B. Bierman; Bierman, Muserlian and Lucas

(57) ABSTRACT

A method for manufacturing a color coupler used in a silver halide photographic light-sensitive material using an ammonium trihalide.

Said method for manufacturing the color coupler comprising the following step:

a step for halogenating a coupling position of a four equivalent coupler using a halogenating agent, wherein said halogenating agent is said ammonium trihalide.

16 Claims, No Drawings

METHOD FOR MANUFACTURING A COLOR COUPLER USED IN A SILVER HALIDE PHOTOGRAPHIC LIGHT-SENSITIVE MATERIAL

FIELD OF THE INVENTION

The present invention relates to a method for manufacturing color couplers used in a silver halide color photographic light-sensitive material by using ammonium trihalide as a halogenation agent, and specifically to a method for manufacturing color couplers with small amounts of by-products and in high yield.

BACKGROUND OF THE INVENTION

In a silver halide color photographic light-sensitive material, an organic compound termed color coupler is used to form a color image. Said silver halide color photographic light-sensitive material contains at least three kinds of silver halide emulsions being photosensitive to blue light, green light and red light, and contains at least three kinds of couplers each corresponding to the three primary colors of light. When said silver halide color photographic light-sensitive material is exposed to light and then processed in developing solution containing a color developing agent, it forms the three colors of yellow, magenta and cyan, which are produced by reaction of an oxidized color developer generated in response to the amount of exposure with three kinds of couplers. By blending pixels of these three colors, all colors in the visible spectrum can be produced.

In these color couplers, in cases where a carbon atom of the couplers reacting with the oxidized color developing agent (this carbon atom being called a coupling-positioned carbon atom) is not substituted by any substituent (active methylene), four silver atoms are theoretically required to form one molecule of dye. On the other hand, in cases where the coupling-positioned carbon atom is substituted by an anionic eliminating group, it is known that two silver atoms are required to form one molecule of dye. The former is termed a four-equivalent coupler, and the latter is termed a two-equivalent coupler. Said two-equivalent coupler generally exhibits high coupling reactivity and is used in many color photographic materials because smaller amount of silver halide is required to obtain the same density of dye, compared to the four-equivalent coupler.

Cited as eliminating groups of the two-equivalent coupler, are a halogen atom, an alkoxy group, a phenoxy group, an alkylthio group, a phenylthio group and a nitrogen-containing heterocyclic group, etc., and combined usage of the two-equivalent couplers containing various eliminating groups is employed in current color photographic light-sensitive materials. Specifically couplers in which the coupling-positioned carbon atom is substituted by a halogen atom, such as a chlorine atom and a bromine atom, etc., is not only useful as a final coupler but also useful as an intermediate to introduce an eliminating group other than the halogen atom to the coupling-positioned carbon atom of the coupler by nucleophilic substitution reaction. For this reason, in manufacturing photographic color couplers, the halogenation reaction process is considered to be very critical.

Various methods for introducing the halogen atom to the photographic color coupler and its intermediate are known. For example, as described in Japanese Patent Publication Open to Public Inspection (hereinafter referred to as JP-A) Nos. 60-55343, 61-57536, it is known that chlorine gas and sulfuryl chloride are reacted in a halogen type solvent.

However, the above mentioned method exhibits problems such as, toxicity of the chlorine gas, sulfurous acid gas and hydrogen chloride gas generated in course of reaction being dispersed into the air, production of by-products caused by acidification in the course of the reaction, and corrosion of the reaction vessel.

With respect to a halagenation agent to overcome these problems, disclosed in JP-A 60-98434 is N-chlorosuccinimide as a chlorination agent for a photographic color coupler. In this case, it is possible to prevent the generation of the sulfurous acid gas and hydrogen chloride gas which is a problem in using sulfuryl chloride, etc., but there have been other problems such as the necessity to remove resultant succinimide after reaction and the high cost of N-chlorosuccinimide.

Further, dihalohydantoin has been recently disclosed for an use to synthesize the photographic color coupler and its intermediate in JP-A Nos., 7-304776, 8-301830, 8-310999, 9-59197 and 9-59250, etc. However, this agent is not sufficiently acceptable in reaction yield, side reaction and cost of the agent. Therefore, more improvement is sought.

SUMMARY OF THE INVENTION

An object of the present invention is to provide a method for manufacturing a halogenated compound useful as a color coupler used in a silver halide color photographic light-sensitive material and its intermediate in high reaction yields, with low side reaction rate and low cost.

DETAILED DESCRIPTION OF THE INVENTION

Above object of the invention could be attained by the following method:

In this invention, when an ammonium trihalide as a halogenation agent was reacted with a color coupler having an active methylene, it was found that a hydrogen atom of the active methylene of said color coupler was substituted by a halogen atom such as a chlorine atom and bromine atom, etc. in high reaction yield compared to a conventional known halogenation agent, and with this halogenation agent, an advantage that an amount of by-products was very little was found. As the ammonium trihalide used in the invention, a compound represented by the following Formula (A) is preferably used.

Formula (A)

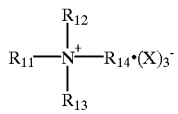

Wherein $R_{11}$, $R_{12}$, $R_{13}$ and $R_{14}$ each represent a hydrogen atom, an alkyl group, an aryl group, a cycloalkyl group and an aralkyl group, and $R_{11}$, $R_{12}$, $R_{13}$ and $R_{14}$ may be the same with each other or different. $R_{11}$, $R_{12}$, $R_{13}$ and $R_{14}$ are each preferably a hydrogen atom, a straight chain or branched alkyl group having 1 to 30 carbon atoms, a cycloalkyl group, a phenyl group and a benzyl group, and more preferable said alkyl group is one having 1 to 16 carbon atoms. X represents a halogen atom and preferable one is a chlorine atom or a bromine atom. Specifically preferable one is a chlorine atom.

Exemplified ammonium trihalides mentioned above used in the invention are shown below, but are not limited thereto.

A-1 $(C_2H_5)_4\overset{+}{N}\ Cl_3^-$

A-2 $(CH_3)_4\overset{+}{N}\ Cl_3^-$

A-3 $(C_4H_9)_4\overset{+}{N}\ Cl_3^-$

A-4 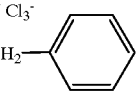

A-5 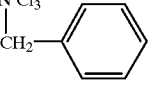

A-6 $(nC_3H_7)_4\overset{+}{N}\ Cl_3^-$

A-7 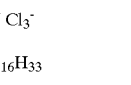

A-8 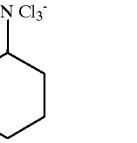

A-9 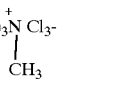

A-10 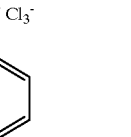

A-11 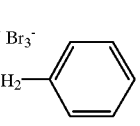

A-12 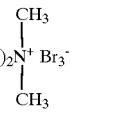

A-13 $(C_2H_5)_4\overset{+}{N}\ Br_3^-$

A-14 $(C_4H_9)_4\overset{+}{N}\ Br_3^-$

A-15 

-continued

A-16 

A-17 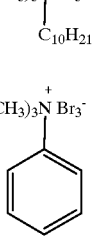

A-18 

A-19 

A-20 (see above)

The above mentioned ammonium trihalide represented by the Formula (A) used in the invention is synthesized by using an inexpensive ammonium halide as a starting raw material.

For example, ammonium trichloride can be synthesized employing a method described in T. Schlama, K. Gabriel, V. Gouverneur and C. Mioskowski, Angew. Chem. Int. Ed. Engl., 36, 2342 (1997), and ammonium tribromide can be syhthesized employing a method described in S. Kajigaeshi, T. Kakinami, M. Moriwaki, S. Fujisaki and T. Okamoto, Bull. Chem. Soc. Jpn., 62, 439 (1989), etc.

Color couplers used in the silver halide photographic light-sensitive material obtained according to the manufacturing method of the invention are compounds characterized in that they have a halogen-substituted active methylene in their molecules which can cause coupling reaction with an oxidized color developing agent resulting in forming dyes for color images.

With regard to the exemplified couplers, one can refer to the disclosure on pages 353–362, fourth edition of "The theory of the photographic process" edited by T. H. James and published by Macmillan Co. in New York in 1977, and on pages 204–222, "Shashin Kogaku no Kiso, Ginen Shashin hen" (Basic Photographic Technology, Silver Halide Photography Compilation) edited by The Society of Photographic Science and Technology of Japan The manufacturing method of the invention is effective in halogenation reaction of the compound other than the compound containing the active methylene group described in the above mentioned references and can be used in halogenating a hydrogen atom of a nitrogen-containing five or six membered aromatic compound ring.

Among the color couplers used in the silver halide photographic light-sensitive material obtained according to the manufacturing method of the invention, a 3-substituted-3-oxo-2-halopropionic acid amide compound represented by the above mentioned Formula (I) is preferably used as a yellow coupler or its intermediate.

As an alkyl group represented by $R_1$, one having 1 to 22 carbon atoms is preferred, for example, are cited a methyl group, an ethyl group, a tert-butyl group, a pentyl group and an octyl group, etc.

As a cycloalkyl group represented by $R_1$, one having 1 to 22 carbon atoms is preferred, for example, are cited a cyclopropyl group, a 1-methylcyclopropyl group, a 1-ethylcyclopropyl group and an adamantyl group, etc.

As an aryl group represented by $R_1$, a phenyl group is preferred.

As a nitrogen-containing heterocyclic group represented by $R_1$, one having 4 to 18 carbon atoms is preferred, for example, are cited a pyrrolyl group, an imidazolyl group, a pyrazolyl group and an indoline-1-yl group, etc.

These groups may contain as a substituent, for example, a halogen atom, a hydroxyl group, a carboxy group, a nitro group, a cyano group, an amino group, an amide group, a carbamoyl group, an alkylsulfonyl group, an arylsulfonyl group, a sulfonamide group, a sufamoyl group, an acyl group and an acyloxy group, etc.

As a substituent represented by $R_2$, for example, are cited a halogen atom, an alkoxy group, a hydroxyl group, a carboxy group, a nitro group, a cyano group, an amino group, an amide group, a carbamoyl group, a sulfonyl group, a sulfonamide group, a sufamoyl group, an acyl group, an ester group and an acyloxy group, etc. Specifically, a chlorine atom, an alkoxy group and an ester group are preferred.

As a halogen atom represented by X, a chlorine atom and bromine atom are preferred.

The exemplified 3-substituted-3-oxo-2-halopropionic acid amide compounds represented by the above mentioned Formula (I) used in the invention are shown below, but are not limited thereto.

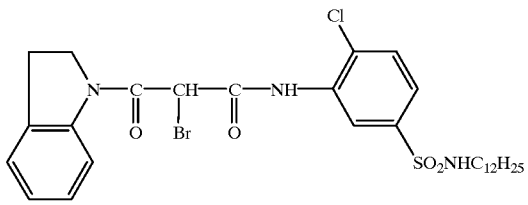
(I-1)

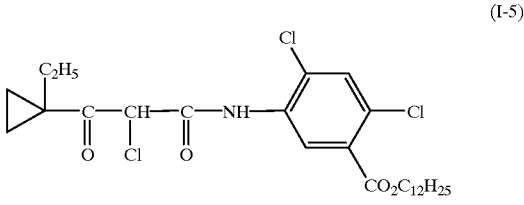
(I-2)

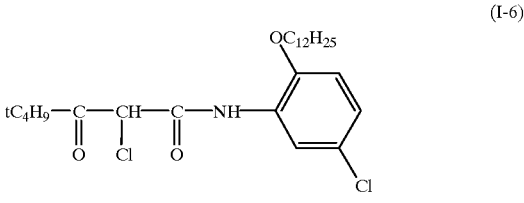
(I-3)

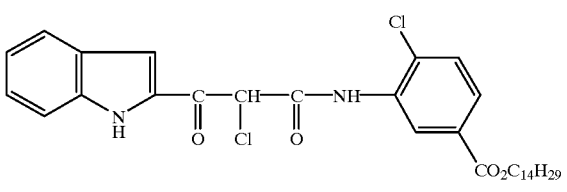
(I-4)

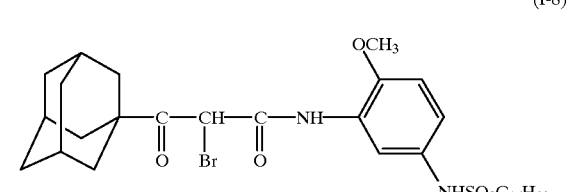
(I-5)

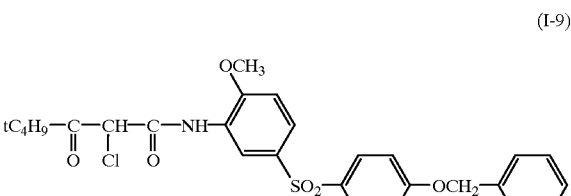
(I-6)

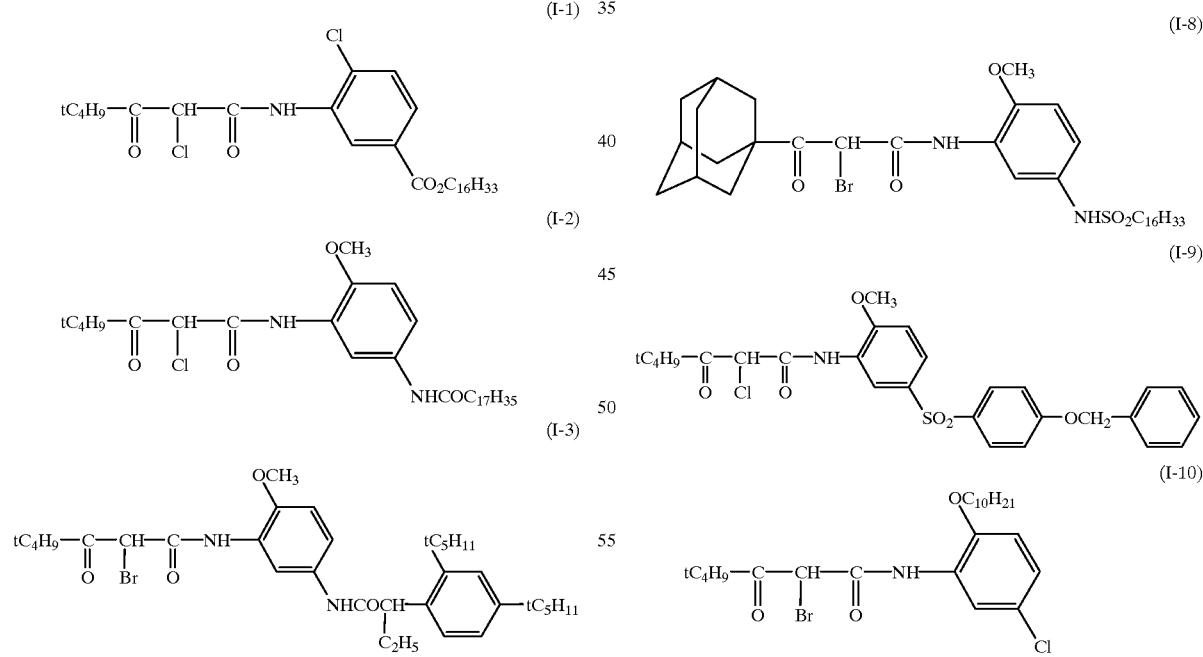

(I-11)
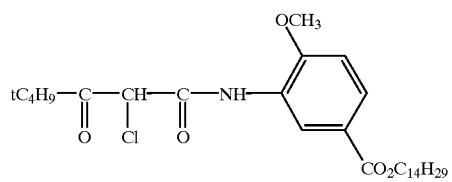

(I-12)
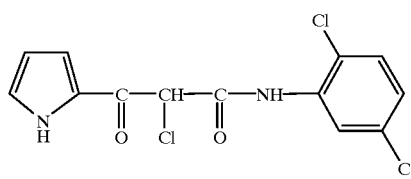

(I-13)
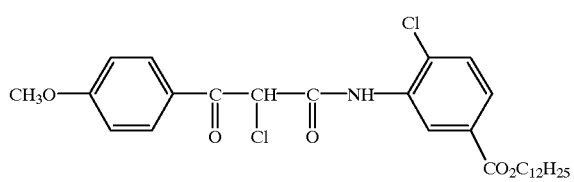

(I-14)
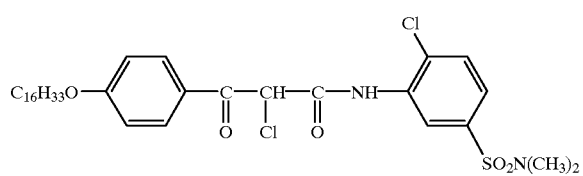

(I-15)
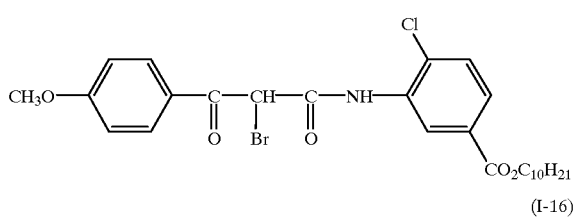

(I-16)
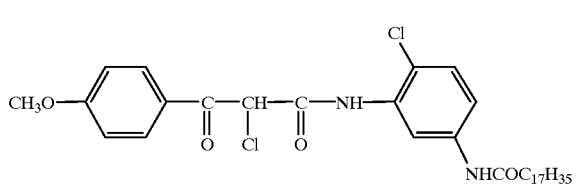

(I-17)
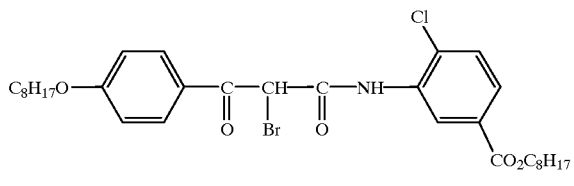

(I-18)
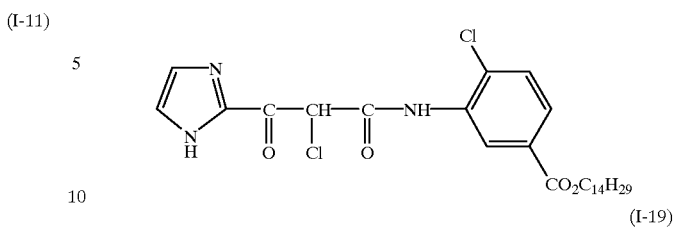

(I-19)

(I-20)
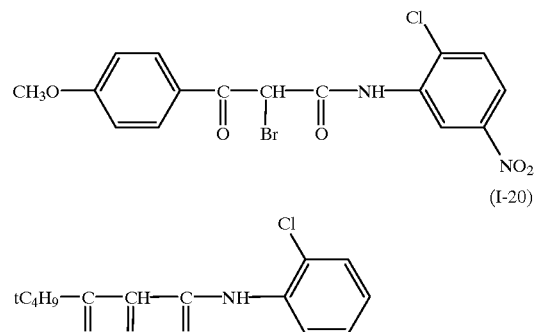

A precursor which is necessary to obtain the compund represented by the above mentioned Formula (I) by halogenating the hydrogen atom of the active methylene of said precursor can be synthesized by using a 3-substituted-oxopropionic acid ester and an aniline derivative. The detailed synthetic way can be referred to U.S. Pat. Nos., 2,875,057 and 3,265,506.

Among the color couplers used in the silver halide photographic light-sensitive material obtained according to the manufacturing method of the invention, a 4-halo-1-substituted-phenylpyrazolo-5-one compound represented by the above mentioned Formula (II) is preferably used as a magenta coupler or its intermediate.

As an alkyl group represented by $R_3$, one having 1 to 22 carbon atoms is preferred, for example, are cited a tert-butyl group, an octyl group and a dodecyl group, a pentadecyl group a hexadecyl group and an octadecyl group, etc.

As an aryl group represented by $R_3$, a phenyl group or a naphthyl group is preferred.

As an acyl group represented by $R_3$, one having 1 to 22 carbon atoms is preferred, for example, are cited a pivaloyl group, a lauroyl group, a mirystoyl group, a stearoyl group, a benzoyl group and a 2-naphthoyl group, etc. Further, these groups may have a substituent.

As a substituent represented by $R_4$, preferred are an alkyl group having 1 to 8 carbon atoms (for example, a methyl group, an ethyl group, a tert-butyl group), a halogen atom (for example, a chlorine atom, bromine atom), a sulfonamide group having 1 to 22 carbon atoms (for example, a methane sulfonamide group, a butane sulfonamide group, a p-toluene sulfonamide group), an acyl group having 1 to 22 carbon atoms (for example, a pivaloyl group, a lauroyl group, a mirystoyl group, a stearoyl group, a benzoyl group, a 2-naphthoyl group and a 2,4-di-tert-pentylphenoxy group), an alkoxy group having 1 to 22 carbon atoms (for example, a methoxy group, an ethoxy group, a buthoxy group, a dodecyloxy group), a sulfonyl group having 1 to 22 carbon atoms (for example, a methane sulfonyl group, an ethane sulfonyl group, a butane sulfonyl group, a phenyl sulfonyl group), etc. Further, these groups may have a substituent.

As a halogen atom represented by X, is preferred a chlorine atom or a bromine atom.

The exemplified 4-halo-1-substituted-phenylpyrazolo-5-one compounds represented by the above mentioned Formula (II) used in the invention are shown below, but are not limited thereto.

(II-1)

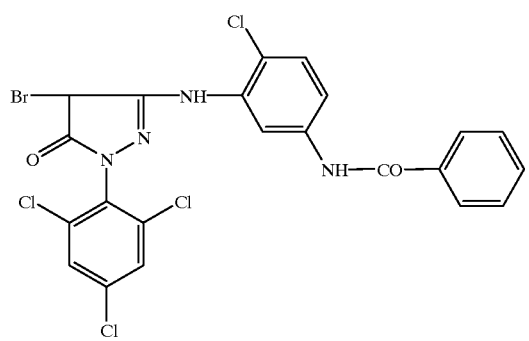

(II-2)

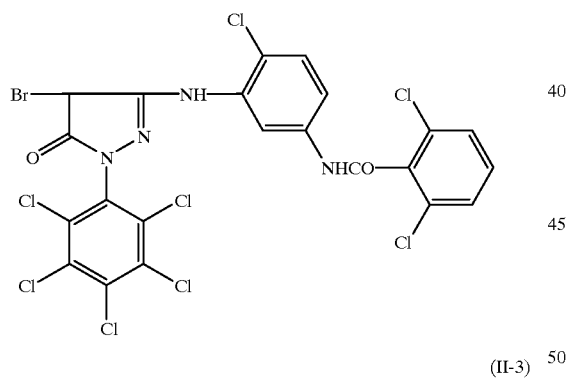

(II-3)

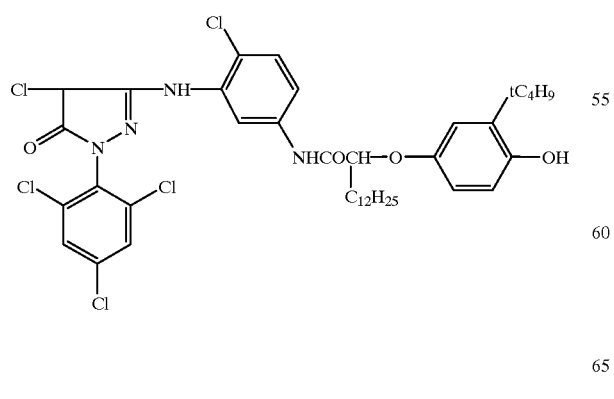

(II-4)

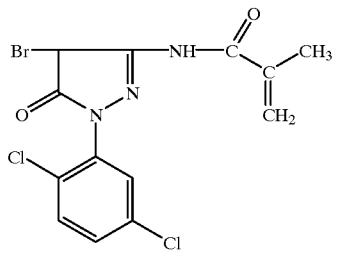

(II-5)

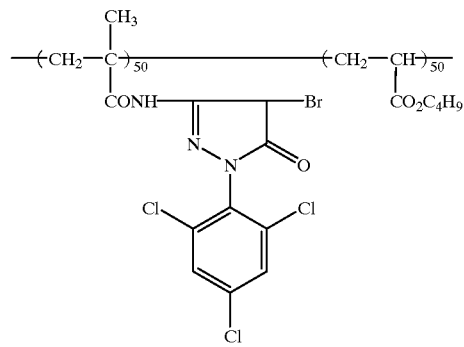

(II-6)

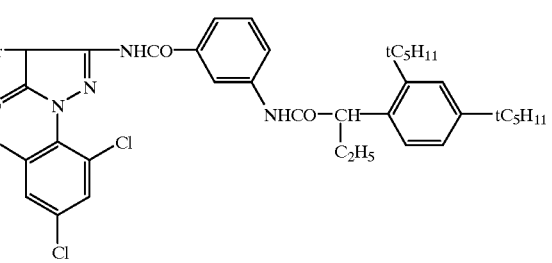

(II-7)

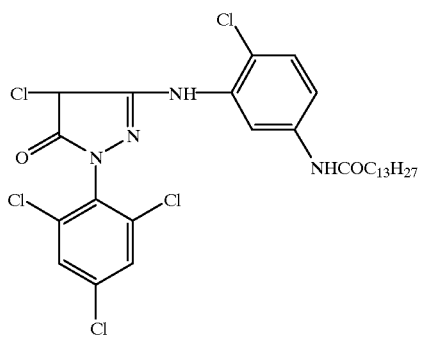

(II-8)

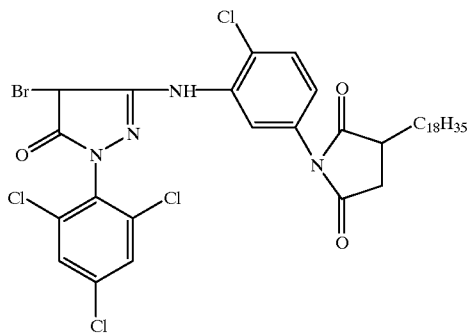

-continued
(II-9) 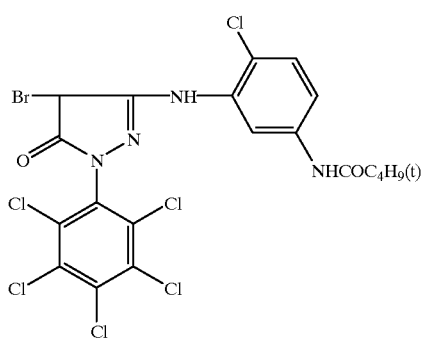
(II-10) 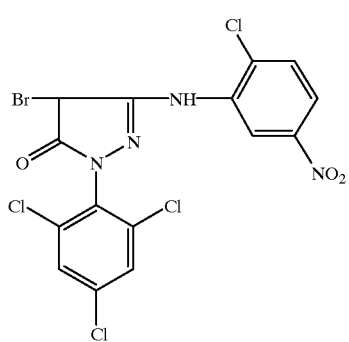
(II-11) 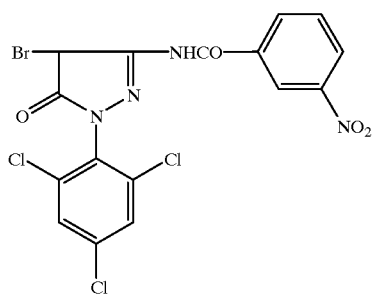
(II-12) 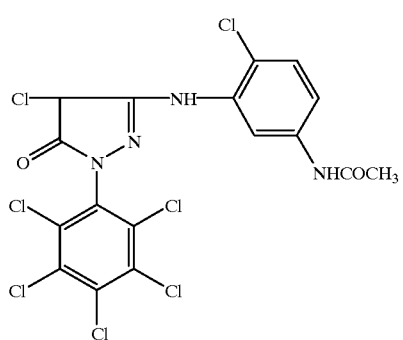
(II-13) 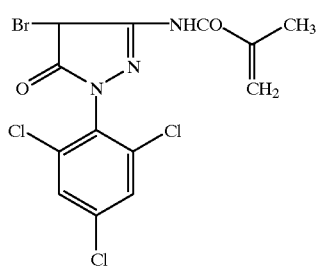
-continued
(II-14) 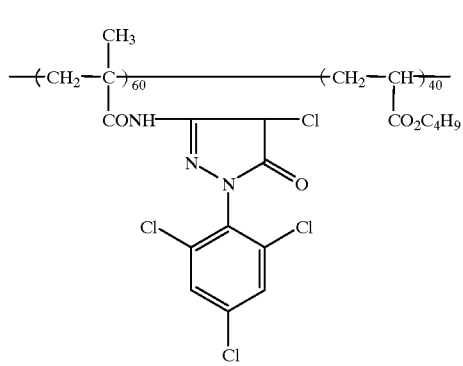
(II-15) 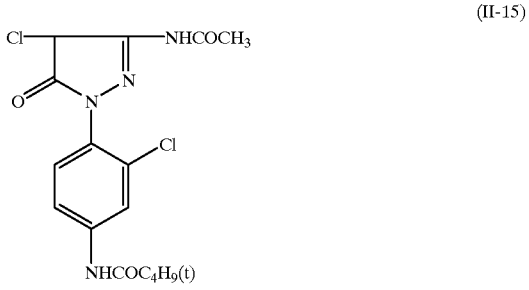
(II-16) 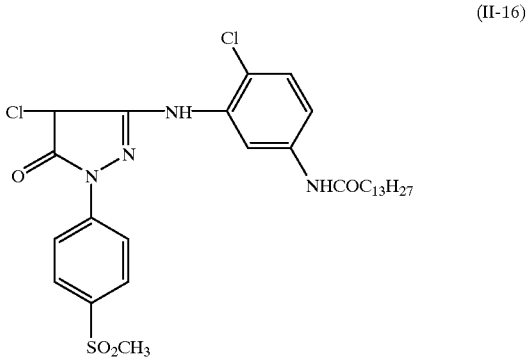
(II-17) 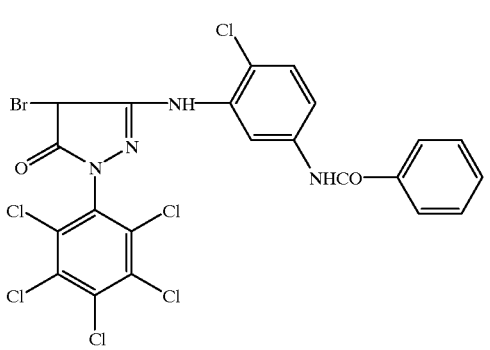
(II-18)

(II-19)

(II-20)

A precursor which is necessary to obtain the compound represented by the above mentioned Formula (II) by halogenating the hydrogen atom of the active methylene of said precursor can be synthesized by referring to U.S. Pat. No. 2,600,788.

Among the color couplers used in the silver halide photographic light-sensitive material obtained according to the manufacturing method of the invention, a halogen-substituted pyrazolotriazole compound represented by the above mentioned Formula (III) is preferably used as a magenta coupler or a cyan coupler or an intermediate of each coupler.

As a substituent represented by R, are cited an alkyl group, an aryl group, an anilino group, an acylamino, a sulfonamide group, an alkylthio group, an arylthio group, an alkenyl group, a cycloalkyl group, a halogen atom, a cycloalkenyl group, an alkynyl group, a heterocyclic group, an alkylsulfonyl group, an arylsulfonyl group, an alkylsulfinyl group, an arylsulfinyl group, a phosphono group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an amide group, an ureide group, a sulfamoylamino group, an alkoxycarbonylamino group, an aryloxycarbonylamino group, an alkoxycarbonyl group, an aryloxycarbonyl group, a heterocyclicthio group, a spiro compound residue group and a bridged hydrocarbon compound residue group.

As an alkyl group represented by R, is preferred one having 1 to 32 carbon atoms of a straight chain or branched chain, and are cited a methyl group, an ethyl group, a tert-butyl group, a pentyl group and an octyl group.

As an aryl group represented by R, a phenyl group is preferred.

As an acylamino group represented by R, are cited an alkylcarbonylamino group and an arylcarbonylamino group.

As a sulfonamide group represented by R, are cited an alkylsulfonylamino group and an arylsulfonylamino group.

As an alkyl component and aryl component in an alkylthio group and arylthio group represented by R, can be cited the above mentioned alkyl groups and aryl group represented by R.

As an alkenyl group represented by R, is preferred one having 2 to 32 carbon atoms, and as a cycloalkyl group, is preferred one having 3 to 12 carbon atoms, specifically preferably 5 to 7, and as an alkenyl group, one which is a straight chain or branched chain may be used.

As a cycloalkenyl group represented by R, is preferred one having 3 to 12 carbon atoms, specifically preferably 5 to 7.

As a phosphoryl group represented by R, are cited an alkyl phosphono group, an alkoxy phosphono group, an aryloxyphosphono group, an arylphosphono group, etc., as an acyl group represented by R, are cited an alkylcarbonyl group, an arylcarbonyl group, etc., as a carbamoyl group represented by R, are cited an alkylcarbamoyl group, an arylcarbamoyl group, etc., as a sulfamoyl group represented by R, are cited an alkylsulfamoyl group, an arylsulfamoyl group, etc., as an acyloxy group represented by R, are cited an alkylcarbonyloxy group, an arylcarbonyloxy group, etc., as a carbamoyloxy group represented by R, are cited an alkylcarbamoyloxy group, an arylcarbamoyloxy group, etc., as an ureide group represented by R, are cited an alkylureide group, an arylureide group, etc., as a sulfamoylamino group represented by R, are cited an alkylsulfamoylamino group, an arylsulfamoylamino group, etc., as a heterocyclic group represented by R, preferred is a 5 to 7 membered heterocyclic ring and concretely are cited a 2-furfuryl group, a 2-thienyl group, a 2-pyrimidinyl group, a 2-benzthiazolyl group, etc., as a heterocyclicoxy group represented by R, preferred is a 5 to 7 membered heterocyclicoxy group and concretely are cited a 3, 4, 5, 6-tetrahydropyranyl-2-oxy group, a 1-phenyltetrazole-5-one group, etc., as a heterocyclicthio group represented by R, preferred is a 5 to 7 membered heterocyclicthio group and concretely are cited a pyridylthio group, a 2-benzthiazolylthio group, 2,4-diphenoxy-1,3,5-triazole-6-thio group, etc., as a siloxy group represented by R, are cited a trimethylsiloxy group, a triethylsiloxy group, a dimethylbutylsiloxy group, etc., as an imide group represented by R, are cited a succinimide group, a 3-heptadecylsuccinimide group, a phthalimide group, a gultarimide group, etc., as a spiro compound residue group, is cited a spiro[3.3]heptane-1-yl group, etc., as a bridged hydrocarbon compound residue group, are cited a bicyclo[2.2.1]heptane-1-yl group, a tricyclo[3.3.1.13.7]decane-1-yl group, a 7,7-dimethyl-bicyclo[2.2.1]heptane-1-yl group, etc.

As a halogen atom represented by X, are preferred a chlorine atom and a bromine atom.

Among the halogen substituted pyrazolotriazole compounds represented by the Formula (III), preferably usable ones are the compounds represented by the following Formula (III-a) to (III-g).

Formula (III-a)

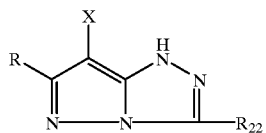

Formula (III-b)

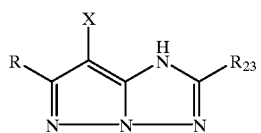

Formula (III-c)

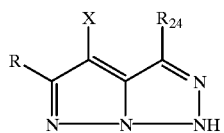

Formula (III-d)

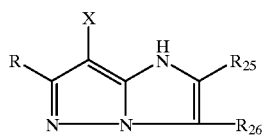

Formula (III-e)

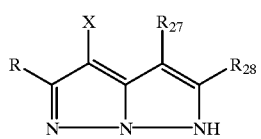

Formula (III-f)

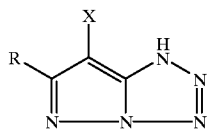

Formula (III-g)

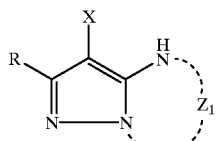

In the above described Formula (III-a) to (III-g), $R_{22}$ to $R_{28}$ are the same as R defined as above.

Among the 7-halopyrazolotriazole compounds represented by the Formula (III-a) to (III-g), specifically preferable ones are the compounds represented by the Formula (III-a) and (III-g).

The exemplified 7-halopyrazoloazole compounds represented by the above Formula (III), (III-a) to (III-g) used in the invention are shown below, but are not limited thereto.

III-1

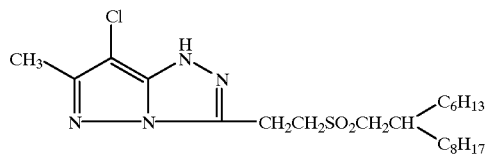

III-2

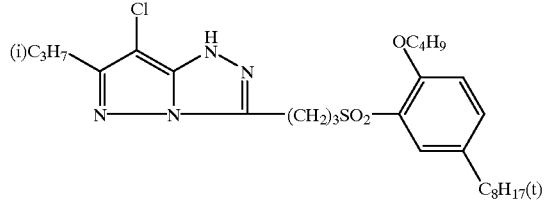

III-3

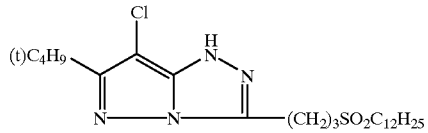

-continued
III-4
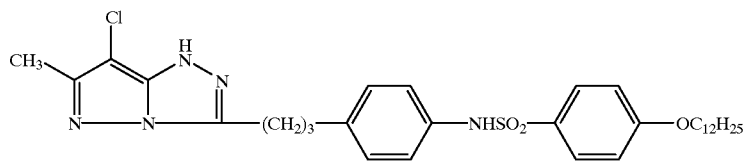
III-5
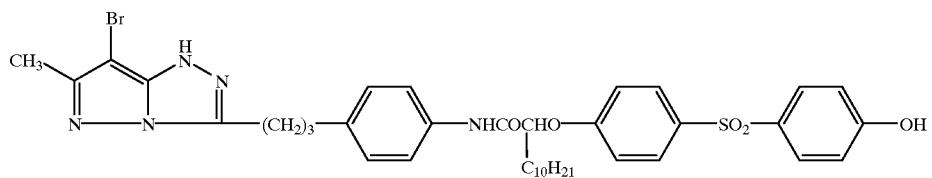
III-6
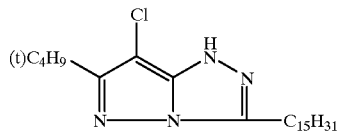
III-7
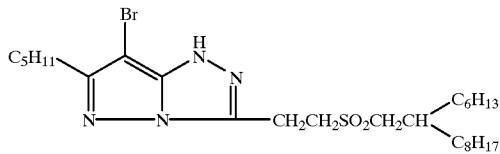
III-8
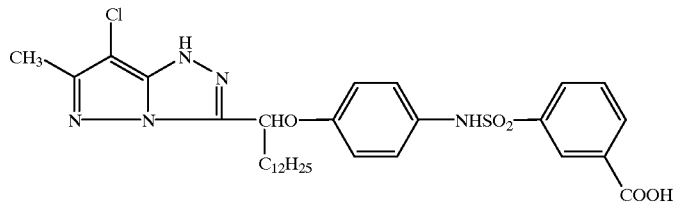
III-9
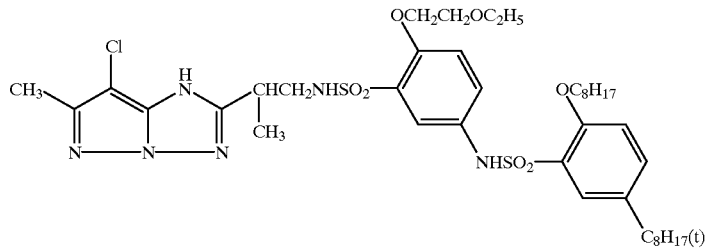
III-10
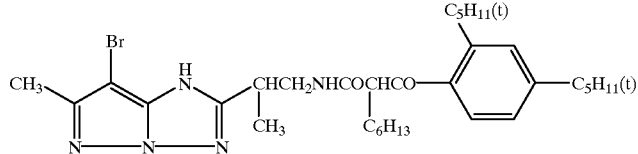

-continued
III-11
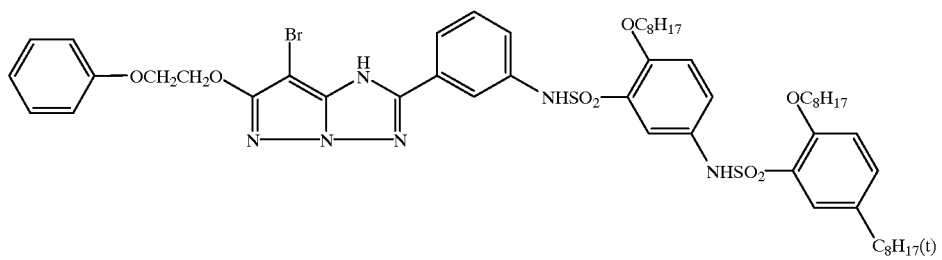
III-12
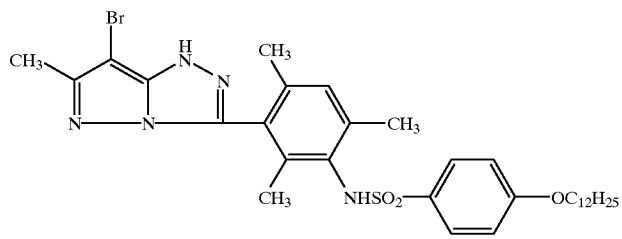
III-13
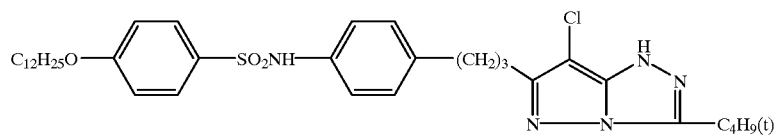
III-14
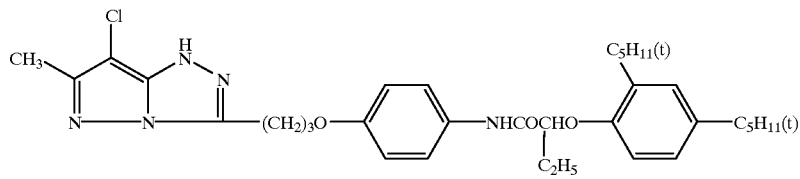
III-15
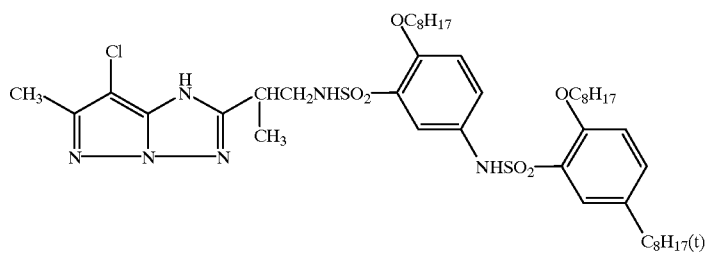
III-16
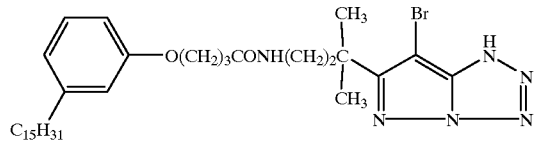
III-17
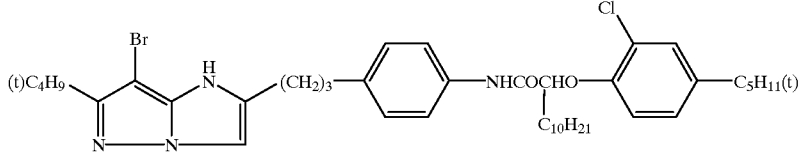

-continued

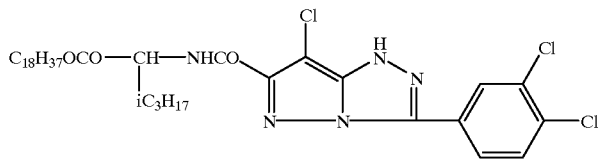

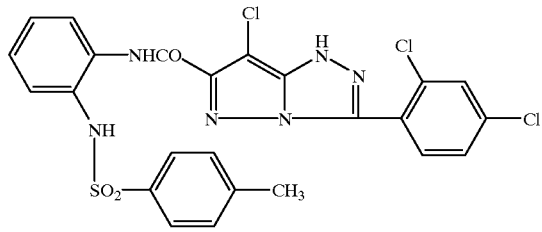

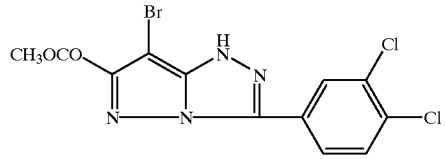

A precursor which is necessary to obtain the compound represented by the above mentioned Formula (III), (III-a) to (III-g) by halogenating the hydrogen atom of the active methylene of said precursor can be synthesized by referring to Journal of the Chemical Society, Perkin I (1977), on pages 2047–2052, U.S. Pat. No. 3,725,067, JP-A Nos., 59-99437, 58-42045, 59-162548, 59-171956, 60-33552, 60-43659, 60-172982, 60-190779, 62-209457 and 63-307453.

Among the color couplers used in the silver halide photographic light-sensitive material obtained according to the manufacturing method of the invention, a 4-halo-1-naphthol compound represented by the above mentioned Formula (IV) is preferably used as a cyan coupler or its intermediate.

As an alkylcarbonyl group represented by $R_5$, one having 2 to 22 carbon atoms is preferred, for example, are cited an acetyl group and a trifluoroacecyl group.

As an arylcarbonyl group represented by $R_5$, one having 7 to 22 carbon atoms is preferred, for example, are cited a benzoyl group, a p-chlorobenzoyl group and a pentafluorobenzoyl group.

As an alkoxycarbonyl group represented by $R_5$, one having 2 to 22 carbon atoms is preferred, for example, are cited a methoxycarbonyl group and an ethoxycarbonyl group and an i-butoxycarbonyl group.

As an aryloxycarbonyl group represented by $R_5$, one having 7 to 22 carbon atoms is preferred, for example, are cited a phenoxycarbonyl group and a naphthoxycarbonyl group.

As an alkylsulfonyl group represented by $R_5$, one having 1 to 22 carbon atoms is preferred, for example, are cited a methanesulfonyl group and an ethanesulfonyl group and a butanesulfonyl group.

As an arylsulfonyl group represented by $R_5$, one having 6 to 22 carbon atoms is preferred, for example, is cited a benzenesulfonyl group.

Further, these groups may have a substituent.

As an alkylamino group represented by $R_6$, one having 1 to 18 carbon atoms is preferred, for example, are cited a methylamino group, an ethylamino group, a butylamino group and a 3-(2,4-di-tert-amylphenoxy)propylamino group.

As an arylamino group represented by $R_6$, one having 1 to 18 carbon atoms is preferred, for example, are cited an anilino group and a naphthylamino group.

As an alkoxy group represented by $R_6$, one having 1 to 18 carbon atoms is preferred, for example, are cited a methoxy group, a butoxy group and a dodecyloxy group.

As an aryloxy group represented by $R_6$, one having 6 to 18 carbon atoms is preferred, for example, are cited a phenoxy group and a naphthyloxy group.

Further, these groups represented by $R_6$ may have a substituent.

As a halogen atom represented by X, are preferred a chlorine atom and a bromine atom.

The exemplified 4-halo-1-naphthol compounds represented by the above Formula (IV) used in the invention are shown below, but are not limited thereto.

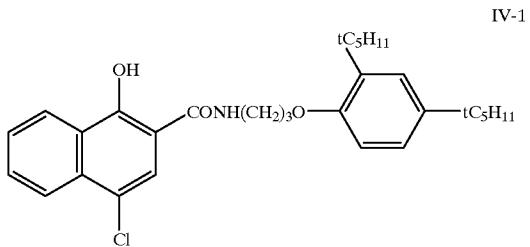

IV-2
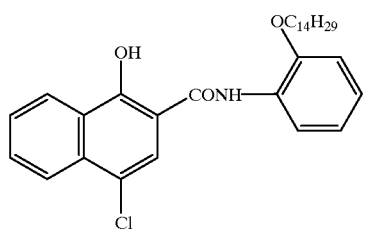
IV-3
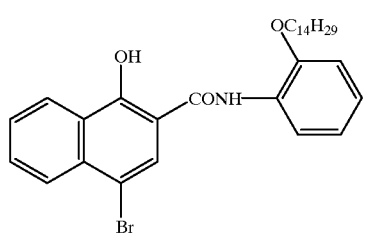
IV-4
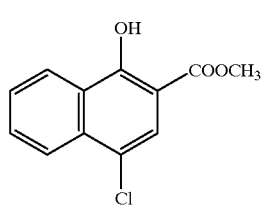
IV-5
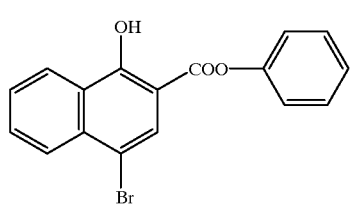
IV-6
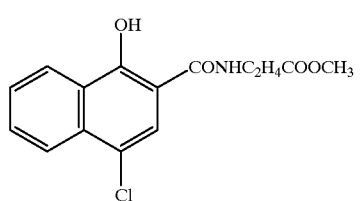
IV-7
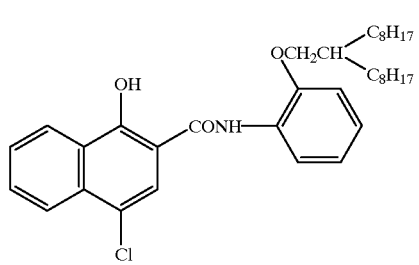
IV-8
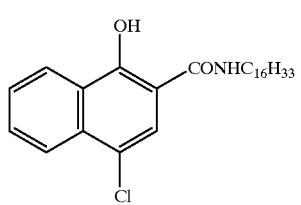
IV-9
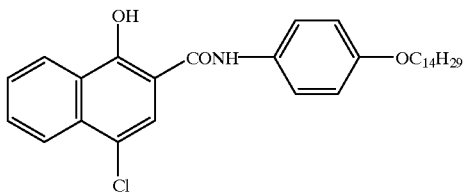
IV-10
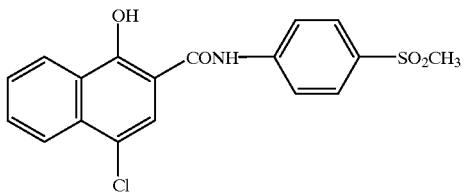
IV-11
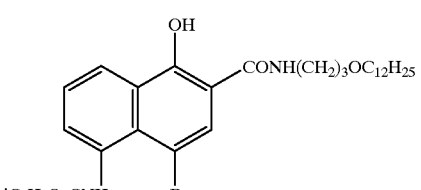
IV-12
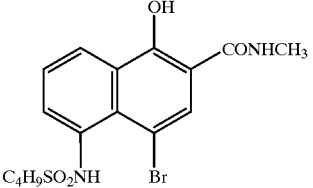
IV-13
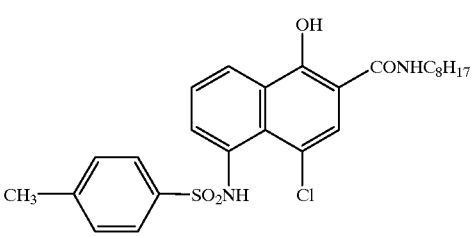
IV-14
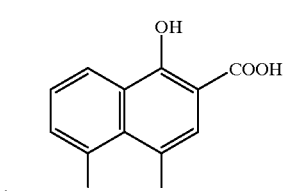
IV-15
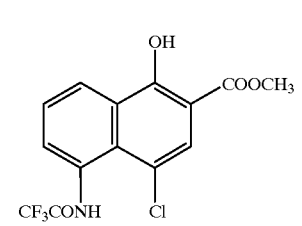

-continued

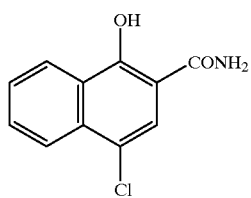
IV-16

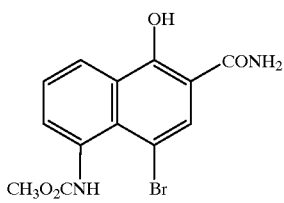
IV-17

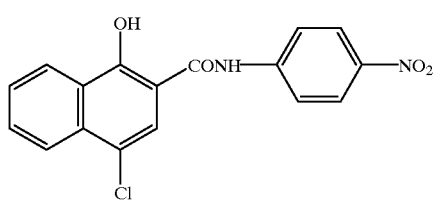
IV-18

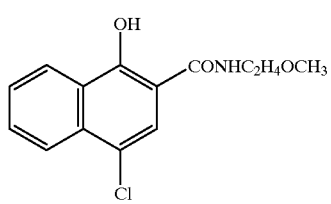
IV-19

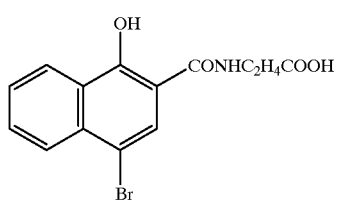
IV-20

A precursor which is necessary to obtain the compound represented by the above mentioned Formula (IV) by halogenating the hydrogen atom of the active methylene of said precursor can be synthesized by referring to JP-A No. 62-123158, Japanese Patent Examined Publication No. 5-21223.

Among the color couplers used in the silver halide photographic light-sensitive material obtained according to the manufacturing method of the invention, a halogenated phenol compound represented by the above mentioned Formula (V) is preferably used as a cyan coupler or its intermediate.

As a substituent represented by $R_7$, are cited an alkyl group, an alkenyl group, a cycloalkyl group, an aralkyl group, an amino group, an alkylamino group, an acylamino group, a nitro group, an alkoxy group, an aryloxy group, a hydroxyl group and a hologen atom, etc.

As an alkyl group represented by $R_7$, for example, are cited a methyl group, an ethyl group, a tert-butyl group and a tert-pentyl group, etc.

As an alkenyl group represented by $R_7$, for example, are cited an ethenyl group and a 2-propenyl group, etc.

As a cycloalkyl group represented by $R_7$, for example, are cited a cyclopropyl group and a cyclohexyl group, etc.

As an aralkyl group represented by $R_7$, for example, is cited a benzyl group.

As an alkylamino group represented by $R_7$, for example, are cited a methylamino group, a tert-butylamino group, a dimethylamino group and a diethylamino group, etc.

As an acylamino group represented by $R_7$, for example, are cited an acetylamino group, a propionylamino group, a pivaloylamino group, an octanoylamino group and a stearoylamino group, etc.

As an alkoxy group represented by $R_7$, for example, are cited a methoxy group, an ethoxy group, a propoxy group and a butoxy group, etc.

As an aryloxy group represented by $R_7$, for example, are cited a phenoxy group and a naphthoxy group, etc.

As a halogen atom represented by $R_7$, for example, are cited a fluorine atom, a chlorine atom and an iodine atom, etc.

The substituting position of a halogen atom represented by X is preferably in 2-, 4- or 6-position relative to the hydroxyl group of the compound represented by the Formula (V), and as the halogen atom, a chlorine atom and a bromine atom are preferred.

The exemplified halogenated phenol compounds represented by the above Formula (V) used in the invention are shown below, but are not limited thereto.

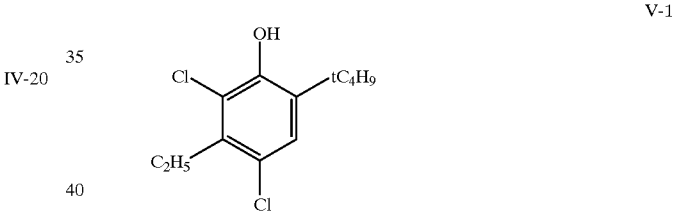
V-1

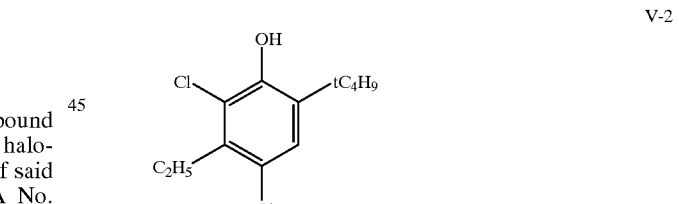
V-2

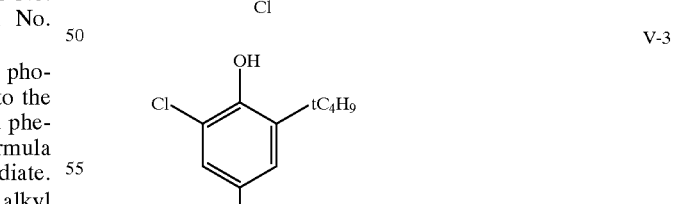
V-3

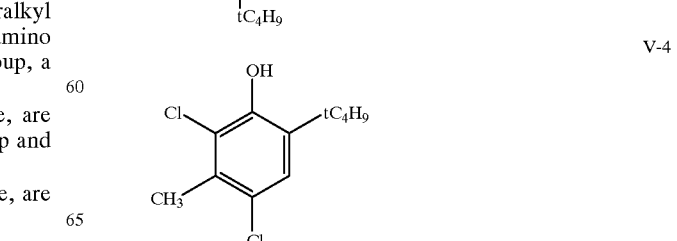
V-4

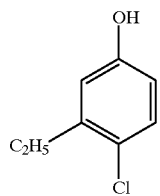 V-5
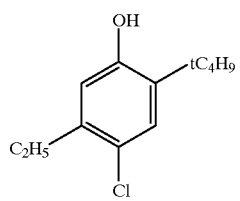 V-6
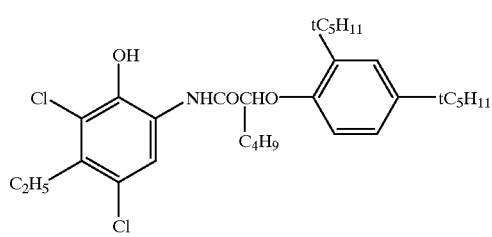 V-7
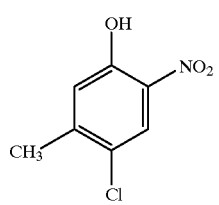 V-8
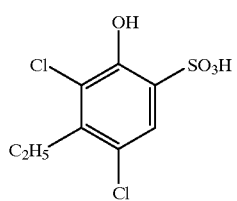 V-9
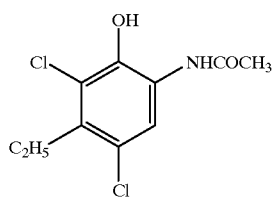 V-10
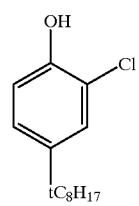 V-11
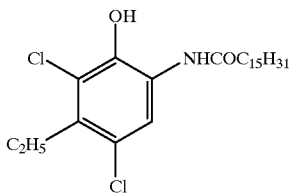 V-12
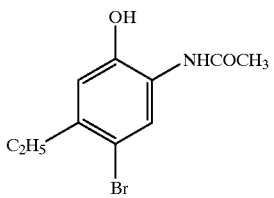 V-13
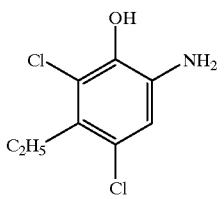 V-14
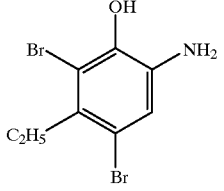 V-15
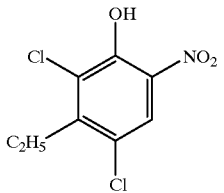 V-16
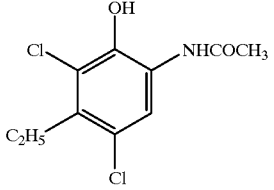 V-17
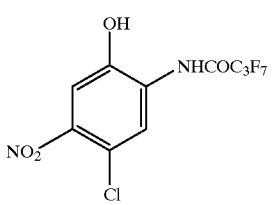 V-18

-continued

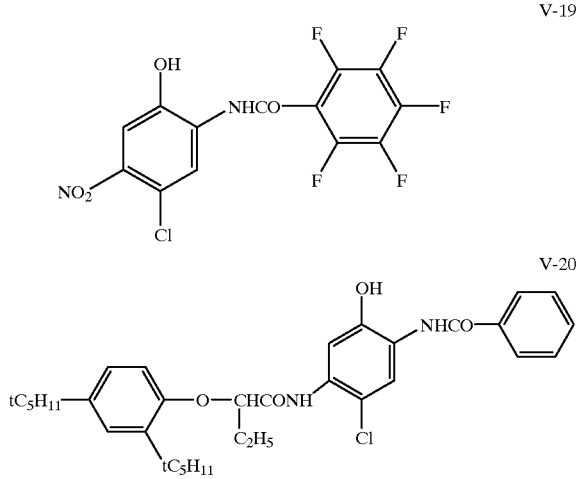

As solvents employed in manufacturing the color couplers usable for the silver halide photographic light-sensitive material used in the invention, are cited a halogen type solvent (for example, chloroform, methylene chloride, ethylene chloride and carbon tetrachloride, etc.), an ester type solvent (for example, ethyl acetate, methyl acetate, butyl acetate, methyl propionate, ethyl propionate, etc.), an aromatic hydrocarbon type solvent (for example, benzene, toluene, xylene, etc.), an aliphatic hydrocarbon type solvent (for example, n-hexane, n-heptane, iso-octane, etc.), an ether type solvent (for example, diethyl ether, di-iso-propyl ether, tetrahydrofuran, dioxane, etc.), a ketone type solvent (for example, acetone, methyl ethyl ketone, methyl iso-butyl ketone, etc.), a nitrile type solvent (for example, acetonitrile, propionitrile, etc.), an alcohol type solvent (for example, methanol, ethanol, n-propanol, iso-propanol, butanol, etc.). Preferable ones are the halogen type solvent, the ester type solvent and the aromatic hydrocarbon type solvent.

These solvents may be used in combination of two kinds or more. An using amount of the solvent used in the invention is preferably 1 to 100 times as much as that of the compound represented by the above mentioned Formula (I) to (V), more preferably 2 to 20 times.

There is no limitation in reaction temperature, but at too low reaction temperature, reaction proceeds slowly, and at too high reaction temperature, decomposition reaction takes place. Therefore, as for the reaction temperature, it is preferably −20 to 100° C., more preferably −10 to 70° C.

An using amount of the ammonium trihalide used in the invention differs depending on a target object, for example, in cases where a mono-halogenated object is obtained, 1.0 mole to 2.0 moles of the ammonium trihalide is preferably used to a mole of the precursor (that is, the four equivalent coupler) of the compound represented by the above mentioned Formula (I) to (V), and in cases where a di-halogenated object is obtained, not less than 2.0 moles of the ammonium trihalide is preferably used to a mole of the precursor (that is, the four equivalent coupler) of the compound represented by the above mentioned Formula (V), more preferably is used 2.2 to 3.0 moles.

EXAMPLES

The present invention is further explained based on examples, but embodiments of the present invention are by no means limited to these examples.

Example 1
(Synthesis of the exemplified compound (I-2))

5.3 g (0.01 mole) of N-{(2-methoxy-5-stearoylamino)phenyl}-α-pivaloylacetic acid amide which was obtained by condensation reaction of 2-methoxy-5-stearoylaminoaniline and ethyl pivaloylacetate in toluene by heating was added to 50 ml of ethyl acetate. To the above obtained solution kept at ice temperature was added 2.8 g (0.012 mole) of tetraethyl ammonium trichloride (A-1), and thus obtained solution was stirred for about 2 hours. After the completion of the reaction, to the resulting solution was added 100 ml of water, and an organic phase separated from an aqueous phase was abstracted. The organic phase was dehydrated with magnesium sulfate and then the organic solvent was removed by evaporation under a reduced pressure to give a residue. The residue was purified through a silica gel chromatography so as to obtain 5.4 g of the target compound (I-2). A reaction yield was 95%. The chemical structure of thus obtained compound (I-2) was confirmed by NMR and mass-spectrum thereof.

Example 2
(Synthesis of the exemplified compound (I-6))

By using 4.4 g (0.01 mole) of N-{(5-chloro-2-dodecyloxy)phenyl}-α-pivaloylacetic acid amide as a starting raw material and 2.8 g (0.012 mole) of tetraethyl ammonium trichloride (A-1), the same reaction as performed in example 1 was carried out so as to produce 4.5 g of the target compound (I-6). The reaction yield was 96%. The chemical structure of thus obtained compound (I-6) was confirmed by NMR and mass-spectrum thereof.

Using N-{(2-methoxy-5-stearoylamino)phenyl}-α-pivaloylacetic acid amide used as a starting raw material in example 1 and N-{(5-chloro-2-dodecyloxy)phenyl}-α-pivaloylacetic acid amide used as a starting raw material in example 2, and using sulfuryl chloride, N-chlorosuccinimide (NCS), and 1,3-dichloro-5,5-dimethylhydantoin (DCH) as chlorinating agents, comparative examples were carried out in a similar manner employed in example 1. Yield of thus obtained target compounds (I-2) and (I-6) is shown in Table 1. Purity examined by a high-performance liquid chromatography is also shown in Table 1.

TABLE 1

| Experimental No. | Target compound | Halogenating agent | Reaction yield (%) | Impurity content (wt %) | Remarks |
| --- | --- | --- | --- | --- | --- |
| 1 | (I-2) | (A-1) | 95 | 1.2 | Inv. |
| 2 | (I-6) | (A-1) | 96 | 1.1 | Inv. |
| 3 | (I-2) | SO$_2$Cl$_2$ | 86 | 5.0 | Comp. |
| 4 | (I-2) | NCS | 81 | 2.4 | Comp. |
| 5 | (I-6) | SO$_2$Cl$_2$ | 80 | 4.3 | Comp. |
| 6 | (I-6) | NCS | 82 | 2.1 | Comp. |
| 7 | (I-6) | DCH | 84 | 3.5 | Comp. |

Inv.: Invention,
Comp.: Comparison

As can be seen from Table 1, the method for manufacturing the color couplers used in the silver halide photographic light-sensitive material according to the invention is excellent in obtaining the target compounds in high yield and with high purity.

Example 3
(Synthesis of the exemplified compound (II-2))

6.5 g (0.01 mole) of 1-(2,3,4,5,6-pentachlorophenyl)-3-[2-chloro-5-(2,6-dichlorobenzamido)]

phenylaminopyrazolo-5-one which is a precursor of the target compound (II-2) was dissolved in 80 ml of acetic acid. To the above obtained solution were added 4.3 g (0.011 mole) of the compound (A-12) according to the invention as a brominating agent and 1.8 g (0.013 mole) of zinc chloride. The reaction mixture was stirred at room temperature for 3 hours. After the orange color of the reaction mixture became lighter, to the reaction mixture was added 30 ml of 5% aqueous solution of sodium hydrogensulfite, thereafter added 50 ml of ethyl acetate and an organic phase separated from an aqueous phase was abstracted. This operation was repeated three times, and total collective organic phase was dehydrated with magnesium sulfate and then the organic solvent was removed by evaporation under a reduced pressure to give a residue. The residue was recrystallized from acetonitrile so as to obtain 6.8 g of the target compound (II-2). The reaction yield was 94%. The chemical structure of thus obtained compound (II-2) was confirmed by NMR and mass-spectrum thereof.

Example 4
(Synthesis of the exemplified compound (II-7))

6.2 g (0.01 mole) of 1-(2,4,6-trichlorophenyl)-3-(2-chloro-5-myristoylamino)phenylaminopyrazolo-5-one which is a precursor of the target compound (II-7) was dissolved in 100 ml of ethyl acetate. To the above obtained solution was added 2.8 g (0.012 mole) of tetraethyl ammonium trichloride (A-1). The reaction solution being kept at ice temperature was stirred for about 4 hours. After the completion of the reaction, to the reaction solution was poured 150 ml of water and then the organic phase separated from an aqueous phase was abstracted. The organic phase was dehydrated with magnesium sulfate and then the organic solvent was removed by evaporation under a reduced pressure to give a residue. The residue was recrystallized from acetonitrile so as to obtain 6.0 g of the target compound (II-7). The reaction yield was 94%. The chemical structure of thus obtained compound (II-7) was confirmed by NMR and mass-spectrum thereof.

Using 1-(2,3,4,5,6-pentachlorophenyl)-3-[2-chloro-5-(2,6-dichlorobenzamido)]phenylaminopyrazolo-5-one used as a starting raw material in example 3 and bromine as a brominating agent, and using 1-(2,4,6-trichlorophenyl)-3-(2-chloro-5-myristoylamino)phenylaminopyrazolo-5-one used as a starting raw material in example 4 and N-chlorosuccinimide (NCS) and 1,3-dichloro-5,5-dimethylhydantoin (DCH) as chlorinating agents, comparative examples were carried out in similar manners employed in example 3 and example 4 respectively so as to obtain the target compounds (II-2) and (II-7). The yield of thus obtained target compounds (II-2) and (II-7) is shown in Table 2. The purity examined by the high speed liquid chromatography is also shown in Table 2.

TABLE 2

| Experimental No. | Target compound | Halogenating agent | Reaction yield (%) | Impurity content (wt %) | Remarks |
|---|---|---|---|---|---|
| 8 | II-2 | (A-12) | 94 | 1.0 | Inv. |
| 9 | II-7 | (A-1) | 92 | 1.1 | Inv. |
| 10 | II-2 | Br$_2$ | 84 | 5.3 | Comp. |
| 11 | II-7 | NCS | 82 | 6.0 | Comp. |
| 12 | II-7 | DCH | 80 | 5.0 | Comp. |

Inv.: Invention,
Comp.: Comparison

As can be seen from Table 2, the method for manufactacturing the color couplers used in the silver halide photographic light-sensitive material according to the invention is excellent in obtaining the target compounds in high yield and with high purity.

Example 5
(Synthesis of the exemplified compound (III-3))

4.3 g (0.01 mole) of 6-tert-butyl-3-(dodecylsulfonylpropyl)-1H-pyrazolo-[5,1-C]-1,2,4-triazole was dissolved in 50 ml of ethyl acetate. To the above obtained solution kept at room temperature was added 1.8 g (0.01 mole) of tetramethyl ammonium trichloride (A-2), and thus obtained solution was stirred for about 3 hours. After the completion of the reaction, the resulting solution was washed, and an organic phase separated from an aqueous phase was abstracted. The organic phase was dehydrated with magnesium sulfate and then the organic solvent was removed by evaporation under a reduced pressure to give a residue. The residue was recrystallized from methanol so as to obtain 4.4 g of the target compound (III-3). The reaction yield was 94%. The chemical structure of thus obtained compound (III-3) was confirmed by NMR and mass-spectrum thereof.

Example 6
(Synthesis of the exemplified compound (III-6))

By using 6-tert-butyl-3-pentadecyl-1H-pyrazolo-[5,1-C]-1,2,4-triazole as a starting raw material, the same reaction as performed in example 5 was carried out so as to produce the target compound (III-6). The reaction yield of the target compound (III-6) was 95%. The chemical structure of thus obtained compound (III-6) was confirmed by NMR and mass-spectrum thereof.

Using 6-tert-butyl-3-(dodecylsulfonylpropyl)-1H-pyrazolo-[5,1-C]-1,2,4-triazole used as a starting raw material in example 5 and 6-tert-butyl-3-pentadecyl-1H-pyrazolo-[5,1-C]-1,2,4-triazole used as a starting raw material in example 6, and using sulfuryl chloride, N-chlorosuccinimide (NCS), and 1,3-dichloro-5,5-dimethylhydantoin (DCH) as chlorinating agents, comparative examples were carried out in a similar manner employed in example 5. The yield of thus obtained target compounds (III-3) and (III-6) is shown in Table 3. The purity examined by the high speed liquid chromatography is also shown in Table 3.

TABLE 3

| Experimental No. | Target compound | Halogenating agent | Reaction yield (%) | Impurity content (wt %) | Remarks |
|---|---|---|---|---|---|
| 13 | III-3 | A-2 | 94 | 1.3 | Inv. |
| 14 | III-6 | A-2 | 95 | 1.0 | Inv. |
| 15 | III-3 | SO$_2$Cl$_2$ | 75 | 5.8 | Comp. |
| 16 | III-3 | NCS | 82 | 7.8 | Comp. |
| 17 | III-6 | SO$_2$Cl$_2$ | 73 | 6.6 | Comp. |
| 18 | III-6 | NCS | 84 | 8.1 | Comp. |
| 19 | III-6 | DCH | 82 | 6.0 | Comp. |

Inv.: Invention,
Comp.: Comparison

As can be seen from Table 3, the method for manfacturing the color couplers used in the silver halide photographic light-sensitive material according to the invention is excellent in obtaining the target compounds in high yield and with high purity.

Example 7
(Synthesis of the exemplified compound (IV-11))

5.2 g (0.01 mole) of 2-(3-dodecyloxypropylcarbamoyl)-5-iso-butoxycarbamido-1-naphthol was dissolved in 30 ml of methylene chloride. To the above obtained solution kept at room temperature was added 4.4 g (0.012 mole) of tetraethyl ammonium tribromide (A-13), and thus obtained solution was stirred for about 2 hours. After the completion of the reaction, to the resulting solution was added water and an organic phase separated from an aqueous phase was abstracted. The organic solvent was removed by evaporation under a reduced pressure to give a residue. The residue was recrystallized from acetonitrile so as to obtain 5.7 g of the target compound (IV-11). The reaction yield was 95%. The chemical structure of thus obtained compound (IV-11) was confirmed by NMR and mass-spectrum thereof.

The bromination reaction was carried out using the same starting raw material as used in example 7 and using bromine as a brominating agent. Thus the comparative example was performed in a similar manner employed in example 7. This reaction produced the target compounds (IV-11) in low reaction yield of 78%, and moreover many by-products such as a di-brominated compound, etc. were proved to be produced. In cases where N-bromosuccinimide was employed as the brominating agent, the reaction yield was prove to be insufficient because it was 80%.

Example 8
(Synthesis of the exemplified compound (V-20))

5.3 g (0.01 mole) of 2-benzamido-5-(2,4-di-tert-pentylphenoxy)butylamidophenol was dissolved in 100 ml of ethyl acetate. To the above obtained solution was added 2.8 g (0.012 mole) of the chlorinating agent (A-1), and thus obtained solution was stirred for about 2 hours. After the completion of the reaction, to the resulting solution was added water and an organic phase separated from an aqueous phase was abstracted. The organic phase was dehydrated with magnesium sulfate and then organic solvent was removed by evaporation under a reduced pressure to give a residue. The residue was recrystallized from acetonitrile so as to obtain 5.4 g of the target compound (V-20). The reaction yield was 96%. The chemical structure of thus obtained compound (V-20) was confirmed by NMR and mass-spectrum thereof.

The chlorination reaction was carried out using the same starting raw material as used in example 8 and using sulfuryl chloride as a chlorinating agent. Thus the comparative example was performed in a similar manner employed in example 8. This reaction produced the target compounds (V-20) in low reaction yield of 75%, and moreover many by-products were proved to be produced. In cases where N-chlorosuccinimide was employed as the chlorinating agent, the reaction yield was proved to be insufficient because it was 78%.

What is claimed is:

1. A method for synthesizing a silver halide photographic color coupler comprising halogenating at a coupling position of a four equivalent coupler with an ammonium trihalide.

2. The method of claim 1 wherein said four equivalent coupler is represented by Formula (1):

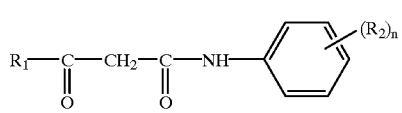

Formula (1)

wherein $R_1$ represents an alkyl group, a cycloalkyl group, an aryl group or a nitrogen-containing heterocyclic group, $R_2$ is a substituent selected from the group consisting of an halogen atom, an alkoxy group, a hydroxyl group, a carboxy group, a nitro group, a cyano group, an amino group, an amide group, a carbamoyl group, a sulfonyl group, a sulfonamide group, a sufamoyl group, an acyl group, an ester group and an acyloxy group, n represents an integer of 0 to 5, when said n is not less than 2, said substituents represented by $R_2$ are the sane or different.

3. The method of claim 1, wherein said four equivalent coupler is represented by Formula (2):

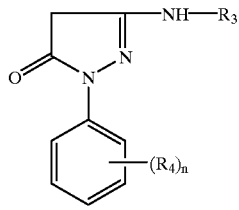

Formula (2)

wherein $R_3$ represents an alky group, an aryl group or an acyl group, $R_4$ is a substituent selected from the group consisting of an alky group having 1 to 8 carbon atoms, a halogen atom, a sulfonamide group having 1 to 22 carbon atoms, an acyl group having 1 to 22 carbon atoms, an alkoxy group having 1 to 22 carbon atoms and a sulfonyl group having 1 to 22 carbon atoms, n represents an integer of 0 to 5; when said n is not less than 2, said substituents represented by $R_4$ are the same or different.

4. The method of claim 1 wherein said four equivalent coupler is represented by Formula (3):

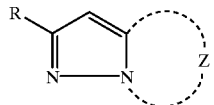

Formula (3)

wherein Z represents non-metal atoms necessary to complete a nitrogen-containing heterocyclic group and R is a substituent selected from the group consisting of an alkyl group, an aryl group, an anilino group, an acylamino group, a sulfonamido group, an alkylthio group, an arylthic group, an alkenyl group, an cycloalkyl group, a halogen atom, a cycloalkenyl group, an alkynyl, a heterocyclic group, an alkylsulfonyl group, an alkylsulfinyl group, an arylsulfinyl group, a phosphono group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an amide group, an ureide group, a sulfamoylamino group, an alkoxycarbonylamino group, an aryloxycarbonylamino group, an alkoxycarbonyl group, an aryloxycarbonyl group, a heterocyclicthio group, a spiro compound group and a bridged hydrocarbon compound group.

5. The method of claim 1 wherein said four equivalent coupler is represented by Formula (4):

Formula (4)

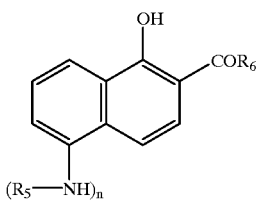

wherein R₅ represents an alkylcarbonyl group, an arylcarbonyl group and an alkoxycarbonyl group, an aryloxycarbonyl group, an alkylsulfonyl group or an arylsulfonyl group, n represents an integer of 0 or 1, R₆ represents an amino group, an alkylamino group, an arylamino group, a hydroxyl group, an alkoxy group or an aryloxy group.

6. The method of claim 1 wherein said four equivalent coupler is represented by Formula (5):

Formula (5)

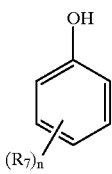

wherein R₇ is a substituent selected from the group consisting of an alkyl group, an alkenyl group, a cycloalkyl group, an aralkyl group, an amino group, an alkylamino group, an acylamino group, a nitro group, an alkoxy group, an aryloxy group, a hydroxy group and a halogen atom, n represents an integer of 1 to 4; when said n is not less than 2, said substituents represented, by R₇ are the same or different.

7. A method for synthesizing a compound represented by Formula (I), (II), (III), (IV) or (V), wherein the method comprises a step of halogenating a coupling position of a compound represented by Formula (1), (2), (3), (4) or (5) corresponding to the compound represented by Formula (I), (II), (III), (IV) or (V), respectively, with an ammonium trihalide wherein the Formulas are as follows:

Formula (I)

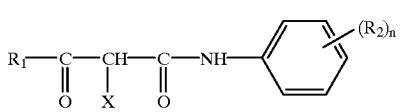

wherein R₁ represents an alkyl group, a cycloalkyl group, an aryl group or a nitrogen-containing heterocyclic group, R₂ is a substituent selected from the group consisting of an halogen atom, an alkoxy group, a hydroxyl group, a carboxy group, a nitro group, a cyano group, an amino group, an amide group, a carbamoyl group, a sulfonyl group, a sulfonamide group, a sulfamoyl group, an acyl group, an ester a group and an acyloxy group, n represents an integer of 0 to 5; when said n is not less than 2, said substituents represented by R₂ are the same or different and X represents a halogen atom;

Formula (II)

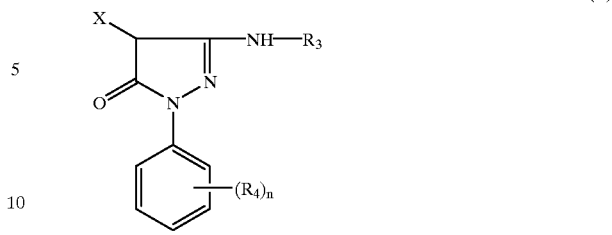

wherein R₃ represents an alkyl group, an aryl group or an acyl group, R₄ is a substituent selected from the group consisting of an alkyl group having 1 to 8 carbon atoms, a halogen atom, a sulfonamide group having 1 to 22 carbon atoms, an acyl group having 1 to 22 carbon atoms, an alkoxy group having 1 to 22 carbon atoms and a sulfonyl group having 1 to 22 carbon atoms, n represents an integer of 0 to 5; when said n is not less than 2, said substituents represented by R₄ are the name or different and X represents a halogen atom;

Formula (III)

wherein Z represents non-metal atoms necessary to complete a nitrogen-containing heterocyclic group, R is a substituent selected from the group consisting of an alkyl group, an aryl group, an anilino group, an acylamino group, a sulfonamide group, an alkylthio group, an arylthio group, an alkenyl group, an cycloalkyl group, a halogen atom, a cycloalkenyl group, an alkynyl, a heterocyclic group, an alkylsulfonyl group, an alkylsulfinyl group, an arylsulfinyl group, a phosphono group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an amide group, an ureide group, a sulfamoylamino group, an alkoxycarbonylamino group, an aryloxycarbonylamino group, an alkoxycarbonyl group, an aryloxycarbonyl group, a heterocyclicthio group, a spiro compound group and a bridged hydrocarbon compound group, and X represents a halogen atom;

Formula (IV)

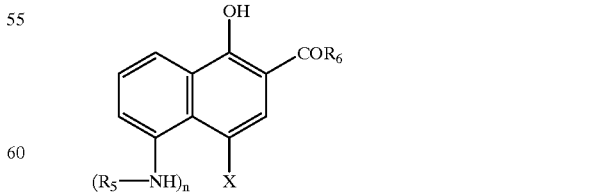

wherein R₅ represents an alkylcarbonyl group, an arylcarbonyl group or an alkoxycarbonyl group, an aryloxycarbonyl group, an alkylsulfonyl group or an arylsulfonyl group, n represent an integer of 0 or 1, R₆ represents an amino group, an alkylamino group, an arylamino group, a hydroxyl group, an alkoxy group or an aryloxy group, and X represents a halogen atom;

Formula (V)

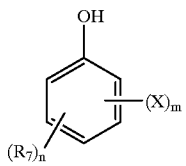

wherein $R_7$ is a substituent selected from the group consisting of an alkyl group, an alkenyl group, a cycloalkyl group, an aralkyl group, an amino group, an alkylamino group, an acylamino group, a nitro group, an alkoxy group, an aryloxy group, a hydroxyl group and a halogen atom, n represents an integer of 1 to 4; when said n is not less than 2, said substituents represented by $R_7$ are the same or different, and X represents a halogen atom, m represents an integer of 1 to 3; when m is not less than 2, the halogen atoms represented by X are the same or different;

Formula (1)

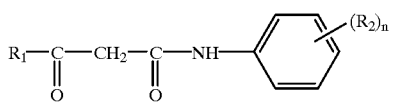

wherein $R_1$ represents an alkyl group, a cycloalkyl group, an aryl group or a nitrogen-containing heterocyclic group, $R_2$ is a substituent selected from the group consisting of an halogen atom, an alkoxy group, a hydroxyl group, a carboxy group, a nitro group, a cyano group, an amino group, an amido group, a carbamoyl group, a sulfonyl group, a sulfonamide group, a sulfamoyl group, an acyl group, an ester group and an acyloxy group; n represents an integer of 0 to 5; when said n is not less than 2, said substituents represented by $R_2$ are the same or different;

Formula (2)

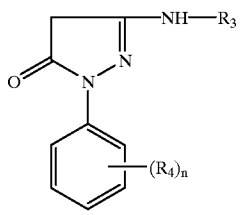

wherein $R_3$ represents an alkyl group, an aryl group or an acyl group, $R_4$ is a substituent selected from the group consisting of an alkyl group having 1 to 8 carbon atoms, a halogen atom, a sulfonamido group having 1 to 22 carbon atoms, an acyl group having 1 to 22 carbon atoms, an alkoxy group having 1 to 22 carbon atoms and a sulfonyl group having 1 to 22 carbon atoms, n represents an integer of 0 to 5; when said n is not less than 2, said substituents represented by $R_4$ are the same or different;

Formula (3)

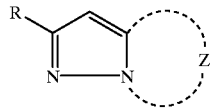

wherein Z represents non-metal atoms necessary to complete a nitrogen-containing heterocyclic group and R is a substituent selected from the group consisting of an alkyl group, an aryl group, an anilino groups an acylamino group, a sulfonamido group, an alkylthio group, an arylthio group, an alkenyl group, an cycloalkyl group, a halogen atom, a cycloalkenyl group, an alkynyl, a heterocyclic group, an alkylsulfonyl group, an alkylsulfinyl group, an arylsulfinyl group, a phosphono group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an amide group, an ureide group, a sulfamoylamino group, an alkoxycarbonylamino group, an aryloxycarbonylamino group, an alkoxycarbonyl group, an aryloxycarbonyl group, a heterocyclicthio group, a spiro compound group and a bridge hydrocarbon compound group;

Formula (4)

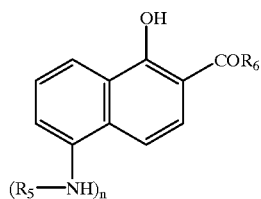

wherein $R_5$ represents an alkylcarbonyl group, an arylcarbonyl group or an alkoxycarbonyl group, an aryloxycarbonyl group, an alkylsulfonyl group or an arylsulfonyl group, n represents an integer of 0 to 1, $R_6$ represents an amino group, an alkylamino group, an arylamino group, a hydroxyl group, an alkoxy group or an aryloxy group;

Formula (5)

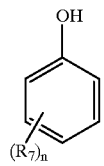

wherein $R_7$ is a substituent selected from the group consisting of an alkyl group, an alkenyl group, a cycloalkyl group, an aralkyl group, an amino group, an alkylamino group, an acylamino group, a nitro group, an alkoxy group, an aryloxy group, a hydroxyl group and a halogen atom, n represents an integer of 1 to 4; when said n is not less than 2, said substituent; represented by $R_7$ are the same or different.

8. A method for synthesizing a compound represented by Formula (I), (II), (III), (IV) or (V), wherein the compound in synthesized by a halogenating agent represented by formula (A);

Formula (I)

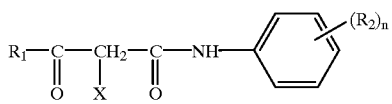

wherein $R_1$ represents an alkyl group, a cycloalkyl group, an aryl group or a nitrogen-containing heterocyclic group, $R_2$ is a substituent selected from tho group consisting of an halogen atom, an alkoxy group a hydroxyl group, a carboxy group, a nitro group, a cyano group, an amino group, an amide group, a carbamoyl group, a sulfonyl group, a sulfonamide group, a sulfamoyl group, an acyl group, an ester group and acyloxy group, n represents an integer of 0 to 5; when said n is not less than 2, said substituents represented by $R_2$ are the same or different and X represents a halogen atom;

Formula (II)

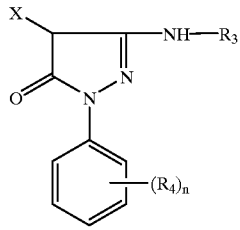

wherein $R_3$ represents an alkyl group, an aryl group or an acyl group, $R_4$ in a substituent selected from the group consisting of an alkyl group having 1 to 8 carbon atoms, a halogen atom, a sulfonamide group having 1 to 22 carbon atoms, an acyl group having 1 to 22 carbon atoms, an alkoxy group having 1 to 22 carbon atom and a sulfonyl group having 1 to 22 carbon atoms; n represents an integer of 0 to 5, when said n is not less than 2, said substituents represented by $R_4$ are the same or different and X represents a halogen atom:

Formula (III)

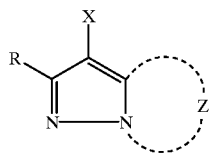

wherein Z represents non-metal atoms necessary to complete a nitrogen-containing heterocyclic group, R is a substituent selected from the group consisting of an alkyl group, an aryl group, an anilino group, an acylamino group, a sulfonamide group, an alkylthio group, an arylthio group, an alkenyl group, an cycloalkyl group, a halogen atom, a cycloalkenyl group, an alkynyl, a heterocyclic group, an alkylsulfonyl group, an alkylsulfinyl group, an arylsulfinyl group, a phosphono group, an acyl group, a carbamoyl group, a sulfamoyl group, a cyano group, an alkoxy group, an aryloxy group, a heterocyclicoxy group, a siloxy group, an acyloxy group, a carbamoyloxy group, an amino group, an alkylamino group, an amide group, an ureide group, a sulfamoylamino group, an alkoxycarbonylamino group, an aryloxycarbonylamino group, an alkoxycarbonyl group, an aryloxycarbonyl group, a heterocyclicthio group, a spiro compound group and a bridged hydrocarbon compound group, and X represents a halogen atom;

Formula (IV)

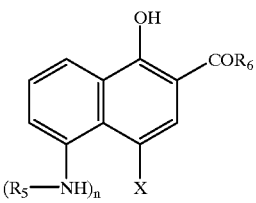

wherein $R_5$ represents an alkylcarbonyl group, an arylcarbonyl group or an alkoxycarbonyl group, an aryloxycarbonyl group, an alkylsulfonyl group or an arylsulfonyl group, n represents an integer of 0 or 1, $R_6$ represents an amino group, an alkylamino group, an arylamino group, a hydroxyl group, an alkoxy group or an aryloxy group, and X represents a halogen atom;

Formula (V)

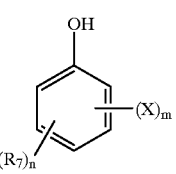

wherein $R_7$ is a substituent selected from the group consisting of an alkyl group, an alkenyl group, a cycloalkyl group, an aralkyl group, an amino group, an alkylamino group, an acylamino group, a nitro group, an alkoxy group, an aryloxy group, a hydroxyl group and a halogen atom, n represents an integer of 1 to 4; when said n is not less than 2, said substituents represented by $R_7$ are the same or different, and X represents a halogen atom, m represents an integer of 1 to 3, when m is not less than 2, the halogen atoms represented by X are the same or different;

Formula (A)

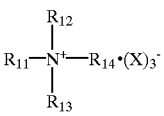

wherein $R_{11}$, $R_{12}$, $R_{13}$ and $R_{14}$ each represent a hydrogen atom, an alkyl group, an aryl group, a cycloalkyl group or an aralkyl group, $R_{11}$, $R_{12}$, $R_{13}$ and $R_{14}$ are the same or different, and X represents a halogen atom.

9. A method of claim 1, wherein the ammonium trihalide is represented by Formula (A), Formula (A)

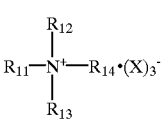

wherein $R_{11}$, $R_{12}$, $R_{13}$ and $R_{14}$ each represent a hydrogen atom, an alkyl group, an aryl group, a cycloalkyl group or an aralkyl group, $R_{11}$, $R_{12}$, $R_{13}$ and $R_{14}$ are the same or different, and X represents a halogen atom.

10. A method of claim 7, wherein the ammonium trihalide is represented by Formula (A), Formula (A)

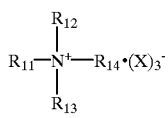

wherein $R_{11}$, $R_{12}$, $R_{13}$ and $R_{14}$ each represent a hydrogen atom, an alkyl group, an aryl group, a cycloalkyl group or an aralkyl group, $R_{11}$, $R_{12}$, $R_{13}$ and $R_{14}$ are the same or different, and X represents a halogen atom.

11. The method of claim 8, wherein the compound is represented by Formula (I).

12. The method of claim 8, wherein the compound is represented by Formula (II).

13. The method of claim 8, wherein the compound is represented by Formula (III).

14. The method of claim 8, wherein the compound is represented by Formula (IV).

15. The method of claim 8, wherein the compound is represented by Formula (V).

16. The method of claim 8, wherein said halogen atom represented by X is a chlorine atom or a bromine atom.

* * * * *